United States Patent
Chang et al.

(10) Patent No.: US 12,023,626 B2
(45) Date of Patent: *Jul. 2, 2024

(54) SYSTEM FOR CAPTURING AND RECYCLING CARBON DIOXIDE IN EXHAUST GAS

(71) Applicant: Korea District Heating Corp., Gyeonggi-do (KR)

(72) Inventors: Won Seok Chang, Gyeonggi-do (KR); Yoon Soo Choi, Gyeonggi-do (KR); Mun Sei Oh, Seoul (KR); Kyung Min Kim, Gyeonggi-do (KR); Ji Hye Yu, Incheon (KR); Young Jae Lee, Daejeon (KR)

(73) Assignee: Korea District Heating Corp., Gyeonggi-do (KR)

(*) Notice: Subject to any disclaimer, the term of this patent is extended or adjusted under 35 U.S.C. 154(b) by 962 days.

This patent is subject to a terminal disclaimer.

(21) Appl. No.: 16/977,961

(22) PCT Filed: Nov. 7, 2018

(86) PCT No.: PCT/KR2018/013429
§ 371 (c)(1),
(2) Date: Sep. 3, 2020

(87) PCT Pub. No.: WO2019/172501
PCT Pub. Date: Sep. 12, 2019

(65) Prior Publication Data
US 2021/0053012 A1    Feb. 25, 2021

(30) Foreign Application Priority Data

Mar. 6, 2018  (KR) .................. 10-2018-0026373

(51) Int. Cl.
*C12M 1/00* (2006.01)
*B01D 53/22* (2006.01)
(Continued)

(52) U.S. Cl.
CPC .......... *B01D 53/75* (2013.01); *B01D 53/229* (2013.01); *B01D 53/62* (2013.01); *B01D 53/84* (2013.01);
(Continued)

(58) Field of Classification Search
None
See application file for complete search history.

(56) References Cited

U.S. PATENT DOCUMENTS

| | | | | |
|---|---|---|---|---|
| 2011/0283618 | A1* | 11/2011 | Martin | C12N 1/12 48/197 R |
| 2013/0064745 | A1* | 3/2013 | Liberman | B01D 53/84 423/220 |
| 2014/0220652 | A1* | 8/2014 | Gonzalez Machii | C12M 35/04 435/292.1 |

FOREIGN PATENT DOCUMENTS

| | | |
|---|---|---|
| JP | 2010-022331 | 2/2010 |
| KR | 10-1122986 | 3/2012 |

(Continued)

OTHER PUBLICATIONS

Document titled "KR101386789B1 Photobioreactor", English machine translation of KR101386789B1 provided by Espacenet (Year: 2014).*
(Continued)

*Primary Examiner* — Holly Kipouros

(57) ABSTRACT

The present invention provides a system for capturing and recycling carbon dioxide in an exhaust gas, which includes a $CO_2$ capture unit into which an exhaust gas containing $CO_2$ is input, and which captures the $CO_2$ as a high concentration enriched gas and separates a first treatment gas; a mineralization process unit which mineralizes the $CO_2$ after receiv-
(Continued)

ing the high concentration enriched gas captured in the $CO_2$ capture unit and discharges a second treatment gas; a mixing tank which receives the first treatment gas and the second treatment gas and mixes them so that the contained $CO_2$ has a predetermined concentration; a photo-culture process unit which receives the resulting third treatment gas from the mixing tank to perform a photo-culture process using microalgae; and a control unit which controls the flow rates and the $CO_2$ contents of the gases supplied and discharged to/from the $CO_2$ capture unit, the mineralization process unit, the mixing tank and the photo-culture process unit.

4 Claims, 4 Drawing Sheets

(51) Int. Cl.
*B01D 53/62* (2006.01)
*B01D 53/75* (2006.01)
*B01D 53/84* (2006.01)
*C01F 5/24* (2006.01)
*C01F 11/18* (2006.01)
*C12M 1/107* (2006.01)

(52) U.S. Cl.
CPC ............... *C01F 5/24* (2013.01); *C01F 11/18* (2013.01); *C12M 21/02* (2013.01); *C12M 21/04* (2013.01); *C12M 43/04* (2013.01); *B01D 2255/802* (2013.01); *B01D 2257/504* (2013.01)

(56) References Cited

FOREIGN PATENT DOCUMENTS

| KR | 10-1334822 | 12/2013 |
| KR | 101386789 B1 * | 4/2014 |
| KR | 10-2018-0000427 | 1/2018 |
| WO | WO 2019/172501 | 9/2019 |

OTHER PUBLICATIONS

International Search Report and the Written Opinion dated Feb. 12, 2019 From the International Searching Authority Re. Application No. PCT/KR2018/013429 and Its Translation of Search Report Into English. (10 Pages).

Jang et al. "Development of Eco-Friendly Compact CCUS (Carbon Capture Utilization Storage) Technology Applicable to Urban Power Plants", 2017 Korean Society for Energy Spring Conference, p. 39, Apr. 14, 2017 & English Translation.

* cited by examiner

SYSTEM FOR CAPTURING AND RECYCLING CARBON DIOXIDE IN EXHAUST GAS

RELATED APPLICATIONS

This application is a National Phase of PCT Patent Application No. PCT/KR2018/013429 having International filing date of Nov. 7, 2018, which claims the benefit of priority of Korean Patent Application No. 10-2018-0026373 filed on Mar. 6, 2018. The contents of the above applications are all incorporated by reference as if fully set forth herein in their entirety.

FIELD AND BACKGROUND OF THE INVENTION

Embodiments relate to a system for capturing and recycling carbon dioxide in an exhaust gas. More particularly, embodiments relate to a system for capturing and recycling carbon dioxide in an exhaust gas, which is able to capture and recycle carbon dioxide in one system by considering the efficiency of each process to maximize the recycling efficiency of carbon dioxide.

With industrial development, the problem of global warming has emerged due to the increase in atmospheric carbon dioxide concentration, and the biggest cause of the increase in carbon dioxide concentration is the use of fossil fuels such as coal, oil and liquefied natural gas, which are used in the energy industry.

From the beginning of the $19^{th}$ century when industrialization began, green gas concentrations such as carbon dioxide ($CO_2$), methane ($CH_4$), nitrogen dioxide, and halocarbons have increased in the atmosphere, and have rapidly increased from the mid-$20^{th}$ century.

As global warming is accelerating due to the increase in greenhouse gases, emission and disposal of these gases are more strictly regulated. Since the United Nations Framework Convention on Climate Change (UNFCCC) held in Rio de Janeiro in June 1992, international interest in global warming is gradually increasing, and an international consensus on greenhouse gas reduction was made, such that developed countries agreed in 2010 to reduce global greenhouse gas emissions by 5.2%, compared to 1990. Particularly, the treatment of $CO_2$ accounting for approximately 80% of greenhouse gases causing global warming has become a more important issue.

Various technologies such as $CO_2$ separation membrane capture technology, $CO_2$ mineralization technology, and photo-culture technology using microalgae are emerging to treat the emitted $CO_2$ component.

However, each technology has an advantage of treating $CO_2$, but also has various problems such as system installation costs, $CO_2$ throughput, and a low $CO_2$ reduction rate per unit area.

Embodiments aim to treat carbon dioxide ($CO_2$) capture and recycle in one linked system by considering the efficiency of each process to maximize $CO_2$ recycling efficiency.

The problems to be solved in the present invention are not limited to the above-described problem, and other problems that are not mentioned herein will be clearly understood by those of ordinary skill in the art.

SUMMARY OF THE INVENTION

One aspect of the present invention may provide a system for capturing and recycling $CO_2$, which includes: a $CO_2$ capture unit into which an exhaust gas containing $CO_2$ is input, and which captures the $CO_2$ at a high concentration as an enriched gas and separates a first treatment gas; a mineralization process unit which mineralizes the $CO_2$ after receiving the high concentration enriched gas captured in the $CO_2$ capture unit and discharges a second treatment gas; a mixing tank which receives the first treatment gas and the second treatment gas and mixes them so that the contained $CO_2$ has a predetermined concentration; a photo-culture process unit which receives the resulting third treatment gas from the mixing tank to perform a photo-culture process using microalgae; and a control unit which controls the flow rates and the $CO_2$ contents of the gases supplied and discharged to/from the $CO_2$ capture unit, the mineralization process unit, the mixing tank and the photo-culture process unit. Preferably, the control unit may control a $CO_2$ concentration in the third treatment gas supplied from the mixing tank to 3 to 7%.

Preferably, the control unit may control a $CO_2$ concentration in the mixing tank by adjusting an inflow amount of the first treatment gas.

Preferably, the enriched gas may be supplied in a liquefied state.

In addition, in still another embodiment of the present invention, the present invention provides a system for capturing and recycling carbon dioxide in an exhaust gas, which includes: an exhaust gas inlet into which an exhaust gas is input and which distributes the gas; a photo-culture process unit which receives the exhaust gas from the exhaust gas inlet to perform a photo-culture process using microalgae and discharge a fourth treatment gas; a mixing tank which receives the exhaust gas from the exhaust gas inlet and the fourth treatment gas and mixes them; a $CO_2$ capture unit which receives the resulting fifth treatment gas from the mixing tank and captures $CO_2$ contained in the fifth treatment gas at a high concentration as an enriched gas; a mineralization process unit which receives the enriched gas captured in the $CO_2$ capture unit to mineralize the $CO_2$, and discharges a sixth treatment gas; and a control unit which controls the flow rates and the $CO_2$ contents of the gases supplied and discharged to/from the exhaust gas inlet, the photo-culture process unit, the mixing tank, the $CO_2$ capture unit and the mineralization process unit, wherein the sixth treatment gas is input into the mixing tank.

The control unit may control an amount of the exhaust gas supplied to the photo-culture process unit through the exhaust gas inlet by considering the $CO_2$ treatment efficiency of the photo-culture process unit.

The control unit preferably controls the $CO_2$ concentration of the mixed gas in the mixing tank to 8 to 10%.

The enriched gas is preferably supplied in a liquefied state.

According to an embodiment, $CO_2$ recycling efficiency can be enhanced.

In addition, the present invention has an effect of compensating for problems of $CO_2$ separation membrane capture technology, $CO_2$ mineralization technology and photo-culture technology using microalgae.

Various and beneficial advantages and effects of the present invention are not limited to those described above, and will be more easily understood during the description of specific embodiments of the present invention.

DESCRIPTION OF SPECIFIC EMBODIMENTS OF THE INVENTION

Figure 1:
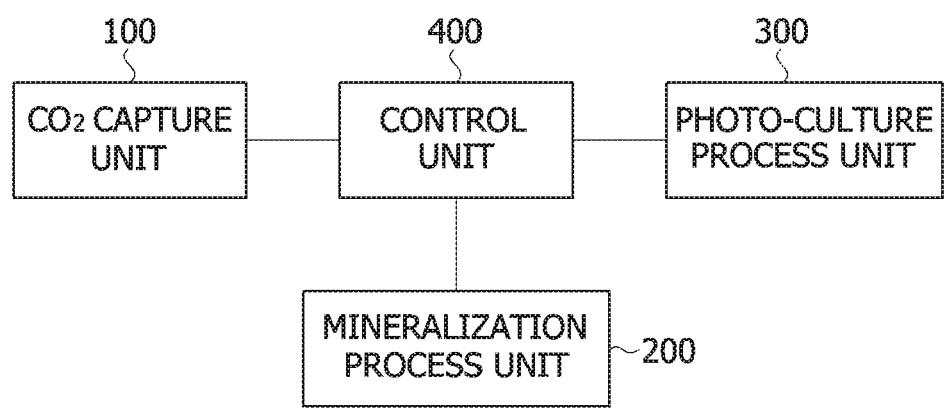
FIG. 1 is a block diagram of a system for capturing and recycling carbon dioxide in an exhaust gas according to an embodiment of the present invention.

The present invention may have various modifications and various examples, and thus specific examples are illustrated in the drawings and described in detail in the detailed description. However, it should be understood that the present invention is not limited to specific embodiments, and includes all modifications, equivalents or alternatives within the idea and technical scope of the present invention.

The ordinal numbers, for example, "first" and "second," may be used to describe various components, but the components should not be limited by these terms. The terms are used only to distinguish one component from another component. For example, without departing from the scope of rights of the embodiments, a second component may be referred to as a first component, and similarly, the first component may be referred to as a second component. The term "and/or" encompasses a combination of a plurality of related items described herein or any one of the plurality of related items described herein.

The terms used in the specification are used only to describe specific examples, not to limit the present invention. Singular expressions include plural expressions unless clearly indicated otherwise in the context. In the specification, it should be understood that the term "include" or "have" is intended to indicate the presence of a characteristic, number, step, action, component or part described in the specification, or a combination thereof, but does not preclude the possibility of the presence or addition of one or more other characteristics, numbers, steps, actions, components, parts or a combination thereof.

In the description of examples, when one element is described to be formed "on or under" another element, the "on or under" includes both cases in which two elements are brought into direct contact with each other or one or more other elements are indirectly disposed between the two elements. In addition, the expression "on or under" may also mean upward and downward based on one element.

Hereinafter, embodiments will be described in detail with reference to the accompanying drawings. However, the same reference numbers will be assigned to the same or corresponding elements regardless of the figure number, and the overlapping descriptions thereof will be omitted.

FIGS. 1 to 4 clearly show major characteristic parts to conceptually and clearly understand the present invention. As a result, various modifications in the diagrams are expected, and the scope of the present invention is not necessarily limited by the specific forms shown in the drawings.

FIG. 1 is a block diagram of a system for capturing and recycling carbon dioxide in an exhaust gas according to an embodiment of the present invention.

In one embodiment of the present invention, the system for capturing and recycling carbon dioxide in an exhaust gas may include a $CO_2$ capture unit 100, a mineralization process unit 200, a photo-culture process unit 300 and a control unit 400.

The $CO_2$ capture unit 100, which constitutes the present invention, may use separation membrane capture technology, and may be effectively used in $CO_2$ capture in a power plant located on a small site in an expensive urban area. However, in the case of the $CO_2$ capture unit 100 using the separation membrane capture technology, it is difficult to secure land for storing the captured $CO_2$, and there is a problem of decreased stability.

The mineralization process unit 200 has advantages of mass-processing $CO_2$ at high speed and semi-permanently treating $CO_2$ by technology for enrichment and mineralization of $CO_2$. However, to maximize a $CO_2$ reduction rate, a high concentration $CO_2$ supply source is needed.

In addition, a photo-culture process unit 300 has an advantage of producing higher value-added useful materials such as astaxanthin, β-carotene, omega 3 and CGF through biological conversion of $CO_2$ by technology of converting $CO_2$ to biomass using microalgae. However, the photo-culture process using microalgae has a problem of a low $CO_2$ reduction rate per unit area due to limitations in photosynthesis efficiency.

The system for capturing and recycling carbon dioxide in an exhaust gas according to an embodiment of the present invention is characterized by a structure that minimizes disadvantages of each constituent and emphasizes advantages thereof.

The $CO_2$ capture unit 100 may separate $CO_2$ from an exhaust gas and produce a high concentration of $CO_2$.

In one embodiment, the $CO_2$ capture unit 100 may use a separation membrane process.

The results of comparing conventional carbon capture and storage (CCS) technology with a separation membrane process are shown below.

TABLE 1

| Classification | Processing time | Construction costs | Operation cost | Capture unit costs | Land area |
| --- | --- | --- | --- | --- | --- |
| CCS process | 2~3 min | 1.1 billion (won) | 1.5 million/yr | $80/tCO_2$ | 500~800 m² |
| Separation membrane process | 15~20 min | 900 million (won) | 0.8 million/yr | $40/tCo_2$ | 80~100 m² |

When $CO_2$ is captured using a separation membrane capturing process, it can be seen that there are benefits in terms of processing time and processing cost, and confirmed that there is also a difference in land area for installing equipment.

In the $CO_2$ capture unit 100, when an exhaust gas enters a hollow fiber module formed of any one of various materials and flows through, various gas components ($N_2$, $O_2$, and $CO_2$) may be captured at a high speed due to a difference in permeation rate.

Figure 2:
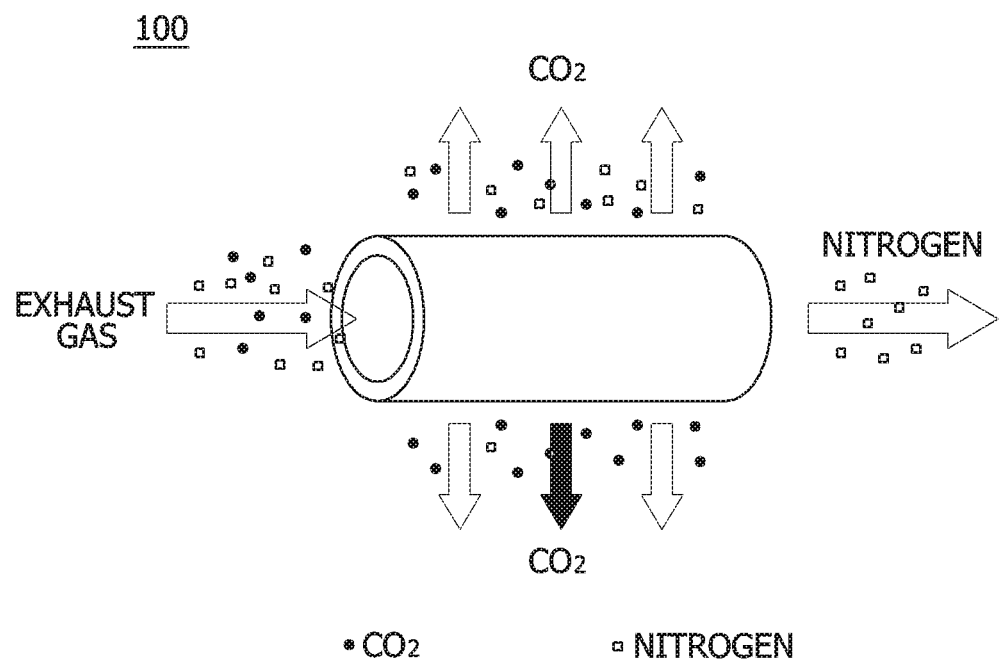
FIG. 2 is a diagram showing an operation when a membrane separation process is used in a $CO_2$ capture unit, which is a constituent of FIG. 1.

FIG. 2 is a diagram showing an operation when a membrane separation process is used in a $CO_2$ capture unit, which is a constituent of FIG. 1, and Table 2 is a table showing relative permeation rates of gases.

TABLE 2

| H$_2$O | H$_2$ H$_0$ CO$_2$ H$_2$S O$_2$ | Ar CO N$_2$ | CH$_4$ |
|---|---|---|---|
| Fast | <-------- Relative permeation rate of gas --------> | | Slow |

Referring to both of FIG. 2 and Table 2, when the exhaust gas is supplied to the separation membrane, CO$_2$ having a relatively high permeation speed is first discharged, and a slow nitrogen gas is later captured. The CO$_2$ capture unit 100 using the membrane separation process may rapidly capture CO$_2$ using such a principle.

In the mineralization process unit 200, a technique of reacting the captured CO$_2$ with a natural mineral or inorganic industrial waste discharged in industry to synthesize a novel mineral.

In one embodiment, the mineralization process unit 200 may produce CaCO$_3$, MgCO$_3$ and a carbonate through mineralization of CO$_2$ in the exhaust gas with Ca and Mg components in construction by-products (slag and waste concrete), thereby permanently solidifying CO$_2$.

The produced carbonate is stable and thus not soluble in water, since CO$_2$ emission to the atmosphere is not possible, there is no harm to the environment, and CO$_2$ is permanently stored to solve the CO$_2$ emission issue.

In the photo-culture process unit 300, a CO$_2$ fixation process may be performed using microalgae. Microalgae, which are phytoplankton, uses sunlight as an energy source, uses photosynthesis for fixing CO$_2$ and thus grows.

The CO$_2$ fixation using the microalgae may use solar energy as a main energy source as in the case in which a plant photosynthesizes CO$_2$, and therefore energy consumption required to fix CO$_2$ is very small.

Microalgae have a higher growth rate than plants, has a biomass productivity per unit area that is 20 to 100-fold higher than the first-generation biofuels such as soybean, corn and rapeseed, is able to be mass-cultured in salt water or wasteland, and is able to utilize various water resources such as sewage and seawater waste. Particularly, there is an advantage that a combustion exhaust gas discharged from a carbon emission source such as a thermal power plant can be directly utilized for cell culture.

The microalgae process can convert CO$_2$ to various higher value-added materials such as biodiesel, a biopolymer, a medicine, health food and a natural pigment, and has an advantage that it is possible to develop an eco-friendly process with a low cost and economic feasibility due to no additional energy input by using solar light.

The microalgae that can be used for photo-culture may include *Neochloris* sp., *Chlorella* sp., *Chlorococcum* sp., *Spirulina* sp., *Haematococcus* sp., *Neospongiococcum* sp., *Scenedesmus* sp., *Dunaliella* sp. and thaustochytrids, but the present invention is not limited thereto. Generally, any microalgae having an ability to convert CO$_2$ to biomass can be used without limitation.

The control unit 400 may control the flow rates and CO$_2$ content of the gases supplied to the CO$_2$ capture unit 100, the mineralization process unit 200 and the photo-culture process unit 300, and control operation of the entire system to enhance the efficiency of the entire process.

Figure 3:
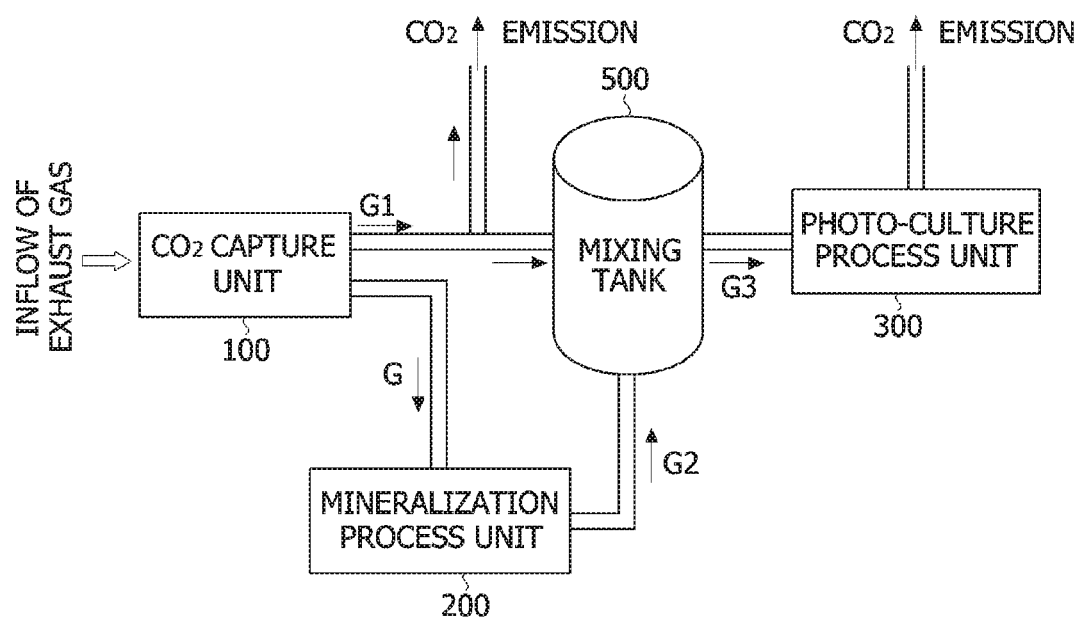
FIG. 3 is a schematic diagram of a first embodiment exhibiting an actual operation of the system of FIG. 1.

FIG. 3 is a schematic diagram of a first embodiment exhibiting an actual operation of the system of FIG. 1.

Referring to FIG. 3, the system for capturing and recycling carbon dioxide in an exhaust gas may include a CO$_2$ capture unit 100 into which an exhaust gas containing CO$_2$ is input, and which captures the CO$_2$ at a high concentration as an enriched gas (G) and separates a first treatment gas (G1), a mineralization process unit 200 which mineralizes the CO$_2$ after receiving the high concentration enriched gas G captured in the CO$_2$ capture unit 100 and discharges a second treatment gas (G2), a mixing tank 500 which receives the first treatment gas (G1) and the second treatment gas (G2) and mixes them so that the contained CO$_2$ has a predetermined concentration, a photo-culture process unit 300 which receives the resulting third treatment gas (G3) mixed in a state of enabling use by microalgae from the mixing tank 500 to perform a photo-culture process using microalgae, and a control unit 400 which controls the flow rates and the CO$_2$ contents of the gases supplied and discharged to/from the CO$_2$ capture unit 100, the mineralization process unit 200, the mixing tank 500 and the photo-culture process unit 300.

The CO$_2$ capture unit 100 captures a high concentration of CO$_2$ from the inflowing exhaust gas using a separation membrane process. Subsequently, the enriched gas (G) is supplied to the mineralization process unit 200, and the first treatment gas (G1) is introduced into the mixing tank 500. The enriched gas (G) may be supplied to the mineralization process unit 200 in the form of a liquefied carbonic acid gas (L-CO$_2$).

The mineralization process unit 200 may produce various types of minerals such as a high calcium material and an aggregate using the high concentration enriched gas (G). The mineralization process unit 200 preferably has a CO$_2$ treatment efficiency of 70 to 80%. The mineralization process unit 200 may supply the second treatment gas (G2) left after mineral production to the mixing tank 500.

The mixing tank 500 receives and mixes the first treatment gas (G1) and the second treatment gas (G2). Here, the control unit 400 may control a CO$_2$ concentration in the third treatment gas (G3) supplied to the photo-culture process unit 300 from the mixing tank 500 to maximize the efficiency of the photo-culture process unit 300. In one embodiment, the CO$_2$ concentration of the third treatment gas (G3) may be controlled to 3 to 7%.

Here, the control unit 400 may control CO$_2$ in the mixing tank 500 by introducing the high concentration second treatment gas (G2) as it is into the mixing tank 500 and adjusting the inflow amount of the first treatment gas (G1). The control unit 400 may discharge a low concentration of the first treatment gas (G1) left after determination of the amount of the first treatment gas (G1) flowing into the mixing tank 500 according to a required concentration to the atmosphere.

The photo-culture process unit 300 receives the third treatment gas (G3) adjusted at an optimal proportion to perform a photo-culture process using microalgae, and after the process, the gas may be discharged into the atmosphere.

In an embodiment, when the inflowing exhaust gas having a CO$_2$ concentration of 8% and a flow rate of 400 m$^3$/hr is supplied, and the CO$_2$ treatment efficiency of the CO$_2$ capture unit 100 is 90%, the enriched gas (G) having a CO$_2$ concentration of 90% may be supplied to the mineralization process unit 200 at a flow rate of 40 m$^3$/hr. Here, the first treatment gas (G1) having a CO$_2$ concentration of 1% may be introduced into the mixing tank 500 at a flow rate of 360 m$^3$/hr.

When the CO$_2$ treatment efficiency of a mineralization apparatus used in the mineralization process unit 200 is 80%, minerals may be produced from the enriched gas (G) having a CO$_2$ concentration of 90%, and the second treatment gas (G2) having a CO$_2$ concentration of 18% may be supplied to the mixing tank 500 at a flow rate of 40 m$^3$/hr.

When the optimal CO$_2$ concentration of the third treatment gas (G3) supplied to the photo-culture process unit 300 is 5%, the control unit 400 adjusts the concentration of the third treatment gas (G3) supplied from the mixing tank 500. In this case, the second treatment gas (G2) having a high $CO_2$ content flow into the mixing tank 500 as it is, and the concentration of the mixing tank 500 may be adjusted by adjusting an inflow amount of the first treatment gas (G1). When the second treatment gas (G2) has a $CO_2$ concentration of 18%, and is supplied at a flow rate of 40 m³/hr, the control unit 400 may adjust the concentration of the third treatment gas (G3) to 5% by adjusting the first treatment gas (G1) having a $CO_2$ concentration of 1%, which has been supplied at a flow rate of 360 m³/hr, to be discharged at a flow rate of 240 m³/hr into the atmosphere and supplied to the mixing tank 500 at a flow rate of 120 m³/hr.

When the photo-culture process unit 300 has a $CO_2$ treatment efficiency of 30%, a gas having a $CO_2$ concentration of 3.5% is discharged into the atmosphere at a flow rate of 160 m³/hr.

In the entire process, when the first treatment gas (G1) discharged into the atmosphere is combined with the gas discharged from the photo-culture process unit 300, the total discharged gas may be discharged into the atmosphere at a flow rate of 400 m³/hr and a $CO_2$ concentration of 2%.

Figure 4:
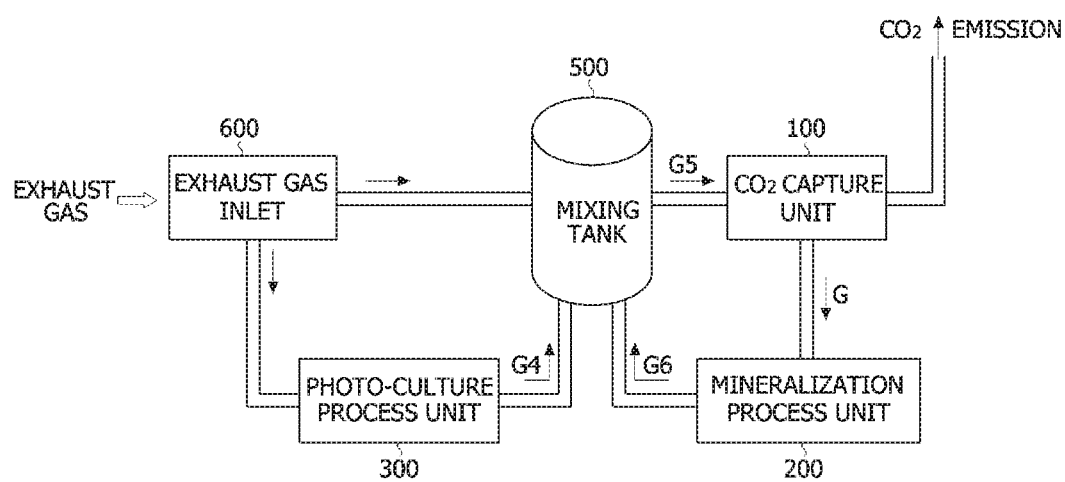
FIG. 4 is a schematic diagram of a second embodiment exhibiting an actual operation of the system of FIG. 1.

FIG. 4 is a schematic diagram of a second embodiment exhibiting an actual operation of the system of FIG. 1.

Referring to FIG. 4, a system for capturing and recycling carbon dioxide in an exhaust gas according to the second embodiment of the present invention may include an exhaust gas inlet 600 into which an exhaust gas is input and which distributes the gas, a photo-culture process unit 300 which receives the exhaust gas from the exhaust gas inlet 600 to perform a photo-culture process using microalgae and discharge a fourth treatment gas (G4), a mixing tank 500 which receives and mixes the exhaust gas from the exhaust gas inlet 600 and the fourth treatment gas (G4), a $CO_2$ capture unit 100 which receives the resulting fifth treatment gas (G5) from the mixing tank 500 and captures $CO_2$ contained in the fifth treatment gas (G5) at a high concentration as an enriched gas (G), a mineralization process unit 200 which receives the enriched gas (G) captured in the $CO_2$ capture unit 100 to mineralize the $CO_2$, and discharges a sixth treatment gas (G6), and a control unit 400 which controls the flow rates and the $CO_2$ contents of the gases supplied and discharged to/from the exhaust gas inlet 600, the photo-culture process unit 300, the mixing tank 500, the $CO_2$ capture unit 100 and the mineralization process unit 200, wherein the sixth treatment gas (G6) is input into the mixing tank 500.

The exhaust gas inlet 600 may distribute an exhaust gas input from an industrial facility to the photo-culture process unit 300 and the mixing tank 500. Here, the control unit 400 may control an amount of the exhaust gas input to the photo-culture process unit 300 in consideration of the concentration of the mixed gas supplied to the $CO_2$ capture unit 100 from the mixing tank 500 by considering the $CO_2$ treatment efficiency of the photo-culture process unit 300. Here, the control unit 400 may adjust the amount of the exhaust gas supplied to the photo-culture process unit 300 by also considering the concentration of the sixth treatment gas (G6) supplied to the mixing tank 500 from the mineralization process unit 200.

The photo-culture process unit 300 may produce biomass by performing a photo-culture process using microalgae after the exhaust gas is received, and the processed fourth treatment gas (G4) may be input to the mixing tank 500.

The mixing tank 500 mixes the exhaust gas which is supplied from the exhaust gas inlet 600, the fourth treatment gas (G4), and the sixth treatment gas (G6) supplied from the mineralization process unit 200, and the mixed gas may be supplied to the $CO_2$ capture unit 100. The $CO_2$ concentration in the mixed gas may be controlled to 8 to 10% by the control unit 400.

The $CO_2$ capture unit 100 captures a high concentration of $CO_2$ from the mixed gas introduced from the mixing tank 500 using a separation membrane process. Afterward, the enriched gas (G) may be supplied to the mineralization process unit 200, and the processed gas may be discharged into the atmosphere. In one embodiment, the enriched gas (G) may be supplied in a liquefied state.

The mineralization process unit 200 may receive the enriched gas (G) from the $CO_2$ capture unit 100 to produce various types of minerals such as a high calcium material and an aggregate. The mineralization process unit 200 preferably has $CO_2$ treatment efficiency of 70 to 80%. The mineralization process unit 200 may supply the sixth treatment gas (G6) left after the mineral production to the mixing tank 500. A cycling procedure is created such that the mineralization process unit 200 processes the enriched gas (G) supplied from $CO_2$ capture unit 100 and inputs the sixth treatment gas (G6) to the mixing tank 500, and the mixing tank 500 recombines the sixth treatment gas (G6) to be supplied to the $CO_2$ capture unit 100.

In one embodiment, when the exhaust gas having a $CO_2$ concentration of 8% is supplied to the exhaust gas inlet 600 at a flow rate of 400 m³/hr, the control unit 400 may supply the gas to the photo-culture process unit 300 having a $CO_2$ treatment efficiency of 30% at a flow rate of 100 m³/hr, and the remainder of the gas may be supplied to the mixing tank 500 at a flow rate of 300 m³/hr.

The photo-culture process unit 300 produces biomass using microalgae, and supplies the fourth treatment gas (G4) having a $CO_2$ concentration of 5.5% and a flow rate of 100 m³/hr to the mixing tank 500.

The mixing tank 500 may mix a gas supplied from the exhaust gas inlet 600, the fourth treatment gas (G4), and the sixth treatment gas (G6) having a $CO_2$ concentration of 18% supplied to the mineralization process unit 200 at a flow rate of 40 m³/hr, and supply the mixed gas having a $CO_2$ concentration of 8 to 10% to the $CO_2$ capture unit 100 at a flow rate of 400 m³/hr.

The $CO_2$ capture unit 100 having a $CO_2$ treatment efficiency of 90% may supply the enriched gas (G) having a $CO_2$ concentration of 90% to the mineralization reaction unit at a flow rate of 40 m³/hr, and the processed gas having a $CO_2$ concentration of 1% may be discharged into the atmosphere at a flow rate of 360 to 400 m³/hr.

In the first embodiment shown in FIG. 3, although the concentration of $CO_2$ finally discharged into the atmosphere is high as 2%, the entire process is sequentially carried out so that the energy consumption is lowered.

However, in the second embodiment shown in FIG. 4, although the concentration of $CO_2$ finally discharged into the atmosphere is low as 1%, to construct a cycling structure of the mineralization reaction unit, the energy consumption increases as compared to the first embodiment.

As above, the embodiments of the present invention have been described in detail with reference to the accompanying drawings.

The above description only exemplifies the technical spirit of the present invention, and it will be understood by those of ordinary skill in the art that the present invention can be modified, altered and substituted in various forms without departing from the essential features of the present invention. Therefore, the embodiments disclosed in the present invention and the accompanying drawings are not intended to limit the technical spirit of the present invention, but to explain the scope of the technical spirit of the present invention. The scope of the present invention is construed with reference to the following claims, and all technical spirit within the equivalent range thereto will be construed as being included in the scope of rights of the present invention.

EXPLANATION OF REFERENCE NUMERALS IN THE DRAWINGS

100: $CO_2$ capture unit, 200: mineralization process unit, 300: photo-culture process unit, 400: control unit, 500: mixing tank, 600: exhaust gas inlet

The invention claimed is:

1. A system for capturing and recycling carbon dioxide in an exhaust gas, comprising:
   an exhaust gas inlet into which an exhaust gas is input and which distributes the gas;
   a photo-culture process unit which receives the exhaust gas from the exhaust gas inlet to perform a photo-culture process using microalgae and discharge a first treatment gas;
   a mixing tank which mixes the exhaust gas from the exhaust gas inlet and the first treatment gas from the photo-culture process unit and discharges a second treatment gas;
   a $CO_2$ capture unit which receives the second treatment gas from the mixing tank and captures $CO_2$ contained in the second treatment gas at a high concentration as an enriched gas;
   a mineralization process unit which receives the enriched gas captured in the $CO_2$ capture unit to mineralize the $CO_2$, and discharges a third treatment gas; and
   a control unit which controls the flow rates and the $CO_2$ contents of the gases supplied and discharged to/from the exhaust gas inlet, the photo-culture process unit, the mixing tank, the $CO_2$ capture unit and the mineralization process unit,
   wherein the third treatment gas is input into the mixing tank.

2. The system of claim 1, wherein the control unit controls an amount of the exhaust gas supplied to the photo-culture process unit through the exhaust gas inlet by considering a $CO_2$ treatment efficiency of the photo-culture process unit.

3. The system of claim 1, wherein the control unit controls the $CO_2$ concentration in the mixing tank to 8 to 10%.

4. The system of claim 1, wherein the enriched gas is supplied in a liquefied state.

* * * * *